United States Patent

Akai et al.

[11] Patent Number: 5,821,127
[45] Date of Patent: Oct. 13, 1998

[54] FLUORESCENT COMPOUNDS AND THEIR USE FOR MEASURING RETICULOCYTES

[75] Inventors: Yasumasa Akai, Miki; Kiminori Miyazaki, Kumamoto; Takashi Sakata, Kakogawa, all of Japan

[73] Assignee: Toa Medical Electronics Co., Ltd., Kobe, Japan

[21] Appl. No.: 726,637

[22] Filed: Oct. 7, 1996

[30] Foreign Application Priority Data

Oct. 6, 1995 [JP] Japan ........................ 7-260346

[51] Int. Cl.⁶ .................................. G01N 31/00
[52] U.S. Cl. .................. 436/10; 436/8; 436/17; 436/18; 436/63; 436/800; 252/408.1
[58] Field of Search .................. 436/8, 10, 17, 436/18, 63, 164, 166, 172, 174, 800; 252/408.1; 435/2, 29, 30, 34, 39; 422/73, 82.05, 82.08

[56] References Cited

U.S. PATENT DOCUMENTS

| | | | |
|---|---|---|---|
| 4,386,146 | 5/1983 | Kishino et al. | 430/95 |
| 4,937,198 | 6/1990 | Lee et al. | 436/94 |
| 4,957,870 | 9/1990 | Lee et al. | 436/63 |
| 5,284,771 | 2/1994 | Fan et al. | 436/10 |
| 5,312,921 | 5/1994 | Glazer et al. | 546/108 |
| 5,321,130 | 6/1994 | Yue et al. | 536/23.1 |
| 5,360,739 | 11/1994 | Fan et al. | 436/63 |
| 5,436,134 | 7/1995 | Haugland et al. | 435/34 |
| 5,534,416 | 7/1996 | Millard et al. | 436/34 |
| 5,563,070 | 10/1996 | Yamamoto et al. | 436/63 |

FOREIGN PATENT DOCUMENTS

63-61622  11/1988  Japan .
WO 94/27146  11/1994  WIPO .

OTHER PUBLICATIONS

Van Bockstaele et al. *Cytometry*, vol. 10, pp. 214–216, 1989.
Derwent Abstract—JP 61 079 163 A, Apr. 22, 1986.
Derent Abstract—JP 62 153 758 A, Jul. 8, 1987.
Patent Abstracts of Japan—JP 08 338839, Dec. 24, 1996.
Thiazole Orange: A New Dye for Reticulocyte Analysis:, Linda G. Lee, et al.; *Cytometry*; 7, pp. 508–517 (1986).
"Flow Cytometric Reticulocyte Analysis", Bruce H. Davis, et al.; *Hematopathology*, vol. 102, (4), pp. 468–477, Oct. 1994.

*Primary Examiner*—Maureen M. Wallenhorst
*Attorney, Agent, or Firm*—Bryan Cave LLP

[57] ABSTRACT

A compound represented by the formula (I):

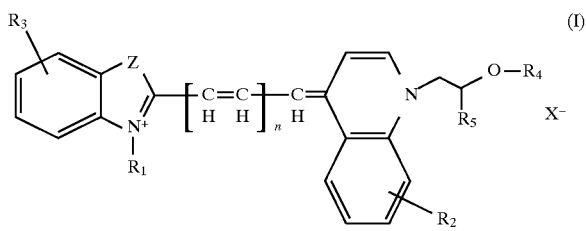

wherein $R_1$ is hydrogen atom or a lower alkyl group; $R_2$ and $R_3$ are independently hydrogen atom, a lower alkyl group or a lower alkoxy groups; $R_4$ is hydrogen atom, an acyl group or a lower alkyl group; $R_5$ is hydrogen atom or an optionally substituted lower alkyl group; Z is sulfur atom, oxygen atom or carbon atom substituted with a lower alkyl group; n is 1 or 2; and $X^-$ is an anion.

13 Claims, 12 Drawing Sheets

FLUORESCENT COMPOUNDS AND THEIR USE FOR MEASURING RETICULOCYTES

BACKGROUND OF THE INVENTION

1. Field of the Invention

The present invention relates to novel fluorescent compounds and use thereof, more particularly to novel fluorescent compounds capable of being used as a fluorescent dye for detecting reticulocytes and measuring a reticulocyte maturation index in clinical test, and also to a reagent containing the compound and a method for measuring reticulocyte using the reagent.

2. Description of Related Art

The reticulocytes are immature erythrocytes immediately after being released into peripheral blood from bone marrow. In the bone marrow, hematopoietic stem cells differentiate and mature to be erythroblastic cells, which then enucleate and are released into the peripheral blood. In the reticulocytes, there remain a small number of organelles such as RNA, ribosomes and mitochondria, which are not contained in mature erythrocytes, as traces of differentiation and maturity of cells.

The classifying and counting of reticulocytes is a great important test for grasping hematopoietic activity in bone marrow of a patient. In blood of a normal human being, the reticulocytes occupies 0.5 to 2.0% of the whole erythrocytes, while the reticulocytes decrease when medullary hemopoiesis is inhibited and they increase when the medullary hemopoiesis is accelerated. For example, the reticulocytes are seen to decrease in a patient suffering from aplastic anemia or treated with chemotherapy against malignant tumor and to increase in a patient suffering from hemolytic anemia.

For classifying and counting reticulocytes in a clinical field, in general, a blood sample is mixed with a dyeing solution containing a basic dye such as New Methylene Blue (NMB) and Brilliant Cresyl Blue (BCB) so that the above-mentioned remaining substances in reticulocytes are precipitated in reticulum, and the reticulocytes are microscopically distinguished from mature erythrocytes and counted (manual method).

The reticulocytes are also classified from the amount of precipitated reticula by conventionally known Heilmeyer classification, which is very useful for grasping hematopoietic kinetics of bone marrow.

However, the above-mentioned manual method is known to have the disadvantages of (1) a complicated sample preparation, (2) the distinction of cells being different among medical technicians and (3) large statistical errors involved due to the small number of the counted cells.

Heilmeyer classification is extremely complicated and therefore it is rarely put in practice although it can provide useful diagnostic information.

To solve these problems, a method for classifying and counting reticulocytes has been proposed in which the reticulocytes are dyed with a fluorescent basic dye capable of specifically dyeing RNA in the reticulocytes, instead of the above-mentioned basic dye, forward scattered light intensity and fluorescence intensity of cells are measured by a flow cytometer, and the reticulocytes are distinguished from erythrocytes mainly based on the difference in the fluorescence intensity.

In this method, Auramine O, which is able to dye the reticulocytes substantially within 30 seconds, is generally used as the basic dye. Reagents and fully automated analyzers for measuring reticulocytes using Auramine O are commercially available from Toa Medical Electronics Co., as Ret Search, R series (R-1000, R-2000, R-3000). Use of such a analyzer can automate and facilitate all steps from preparing a sample to outputting data, avoid the difference in analysis depending on medical technicians, reduce the above-mentioned statistical errors and enable accurate analysis.

The fluorescence intensity of a reticulocyte is known to be in proportion to the amount of RNA remaining in the reticulocyte, that is, in inverse proportion to the maturation of the reticulocyte. Therefore, it is possible to calculate a reticulocyte maturation index (RMI) from the fluorescence intensity. By way of example, FIG. 10 shows a scattergram of reticulocytes measured by an analyzer of the above-mentioned R series. Referring to FIG. 10, the reticulocytes are fractionized into three grades, LFR (Low Fluorescence Ratio), MFR (Middle Fluorescence Ratio) and HFR (High Fluorescence Ratio) from the lowest to the highest in fluorescence intensity. A reticulocyte having a lower fluorescence intensity has a smaller amount of RNA, therefore being maturer. By measuring RMI in this way, diagnostic information similar to Heilmeyer classification can be obtained. Particularly, since the percentage of the youngest reticulocytes (HFR) is known a useful index indicating hemopoietic ability of bone marrow sensitively, for example, for indicating to what extent the hemopoietic ability recovers after a bone marrow transplantation or chemotherapy.

The flow cytometry as described above, though it is very useful, requires a considerably expensive argon laser as a light source exciting fluorescence of the fluorescent dye, and thus the apparatus is disadvantageously expensive and large.

Other fluorescent dyes than Auramine O are Thiazole Orange, Ethidium Bromide and the like as useful for the flow cytometry. These dyes need 5 or more minutes for dyeing reticulocytes. Thiazole Orange, especially, has been reported to need 60 minutes for the dyeing by Lee L. G. et al [Cytometry; 7:508–517(1986)]. For this reason, the sample can hardly be automatically prepared, but must be manually prepared, which presents a problem from the view point of labor saving. Also the obtained data vary with skill or preparator, and, there is a problem that, when blood of a patient is measured by a plurality of laboratories, the laboratories sometimes provide different data. In particular, Davis B. H. et al have reported a large difference in data on RMI of reticulocytes among laboratories in Am. J. Pathol. Vol. 102, (4), 468–477.

On the other hand, there is disclosed in U.S. Pat. No. 5,360,739 a flow cytometer for measuring reticulocytes by measuring the scattered light intensity and either absorbance or fluorescence intensity using a He—Ne laser, which is a relatively inexpensive light source, and Oxazine 750 as a dye. There is described in WO94/271,46 another method for measuring reticulocytes and erythrocytes wherein the erythrocytes are dyed with NMB, then hemocytes are lysed and the reticulocytes in which reticula are precipitated are distinguished from the erythrocytes mainly by the scattered light intensity.

These methods, however, require a lot of time for preparing a sample. Particularly, WO94/271,46 is complicated due to its two specimen preparation steps, which is not suitable for automatization. Moreover since it does not specifically detect RNA of the reticulocytes, the scattered light of the erythrocytes are liable to affect determination results much. In addition, these publications do not disclose RMI at all.

There are disclosed, in Japanese Examined Patent Publication No. Sho 63(1988)-61622 and U.S. Pat. No. 4,957,870, dyes which are designed to bond specifically with RNA which is one of the substances featuring the reticulocytes and increase the fluorescence intensity. However, these publications disclose flow cytometry using a conventional argon laser only, and do not disclose at all methods for measuring reticulocytes using light having a red wavelength as an excitation light source, methods for measuring RMI or reagents used for such methods.

U.S. Pat. No. 5,360,739 describes clearly that the specific binding constant between a dye and the reticulocyte RNA and the rate of penetration of the dye are different for each dye and that it is impossible to predict under what conditions the reticulocytes can be measured.

As described so far, there have been no reagents or methods having all the advantages of being capable of rapidly and accurately measuring reticulocytes and RMI by use of an inexpensive, small-sized light source.

SUMMARY OF THE INVENTION

The present invention provides a fluorecent compound represented by the formula (I):

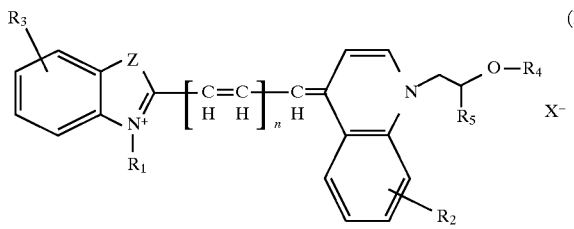

wherein $R_1$ is hydrogen atom or a lower alkyl group; $R_2$ and $R_3$ are independently hydrogen atom, a lower alkyl group or a lower alkoxy group; $R_4$ is hydrogen atom, an acyl group or a lower alkyl group; $R_5$ is hydrogen atom or an optionally substituted lower alkyl group; Z is sulfur atom, oxygen atom or carbon atom substituted with a lower alkyl group; n is 1 or 2; and $X^-$ is an anion.

Further, the present invention provides a reagent for dyeing reticulocytes comprising a compound represented by the formula (I), an multivalent anion for inhibiting non-specific dyeing of erythrocytes and a buffer.

Further, the present invention provides a method for measuring reticulocytes comprising the steps of (i) preparing a sample to be measured by mixing the above reagent for dyeing reticulocytes and a hematological sample;

(ii) introducing the sample to be measured into a flowing system of a flow cytometer provided with a light source emitting red wavelength light to form a sheath flow;

(iii) irradiating the red wavelength light to cells in the sample flowing in the sheath flow;

(iv) measuring scattered light and fluorescence light radiated from the cells to obtain the intensities thereof;

(v) detecting platelets and erythroid cells by the scattered light intensity or by the scattered light intensity and the fluorescence intensity;

(vi) detecting erythrocytes, reticulocytes and leukocytes by the fluorescence intensity or by the fluorescence intensity and the scattered light intensity; and (vii) classifying and counting the platelets, the erythrocytes, the reticulocytes and the leukocytes and calculating the percentages thereof.

Therefore, the present invention provides a novel fluorescent compound enabling accurate determination of reticulocytes using red wavelength light, a reagent using the compound for dyeing reticulocytes and a method for measuring reticulocytes, in order to achieve a low-priced reticulocyte determination technique, that is to achieve a low-priced apparatus, and use of a small-sized semiconductor laser emitting red light.

BREIF DESCRIPTION OF THE DRAWINGS

DESCRIPTION OF THE PREFERRED EMBODIMENTS

Figure 1:
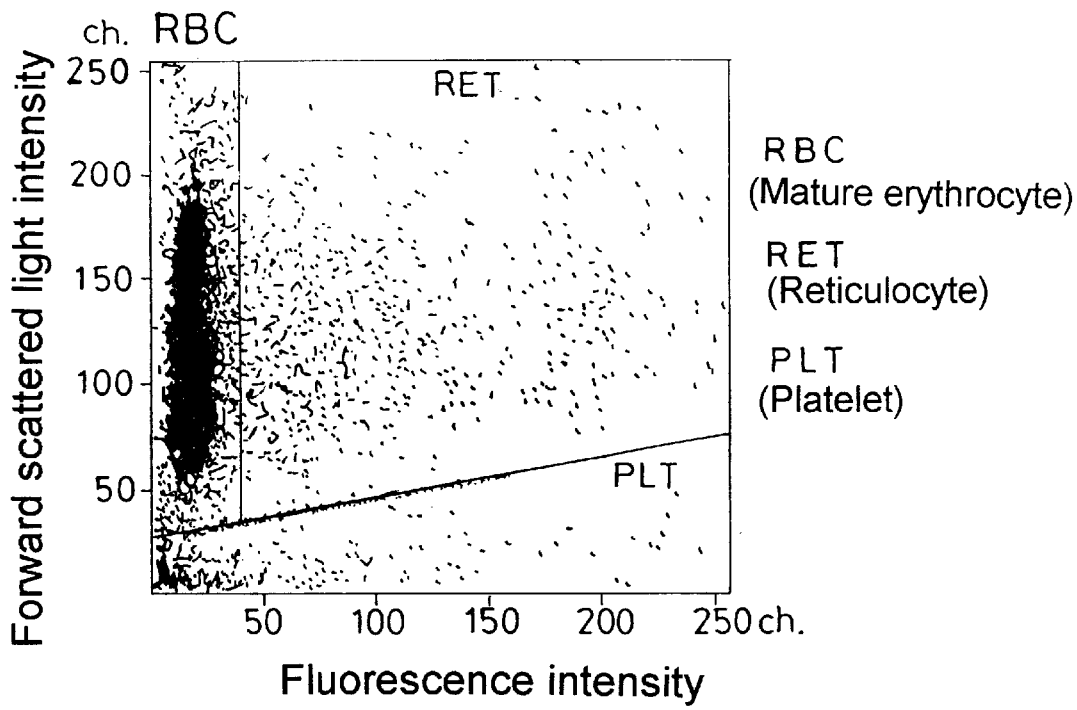
FIG. 1 shows a scattergram of the forward scattered light intensity and the fluorescence intensity of a hematological sample measured using a reagent for dyeing reticulocytes containing the Dye Compound A of the present invention.

The fluorescent compounds of the present invention are those capable of dyeing the reticulocytes and being excited by red wavelength light, and can be used as fluorescent dye.

The lower alkyl group represented by $R_1$ in the formula (I) is a $C_{1-6}$ straight-chain or branched chain alkyl group, including methyl, ethyl, propyl, butyl, isobutyl, sec-butyl, tert-butyl, pentyl and hexyl, among which methyl and ethyl groups are preferred.

The lower alkyl group represented by $R_2$ and $R_3$ is the same as the above-described $R_1$, and the lower alkoxy group represented by $R_2$ and $R_3$ is a $C_{1-6}$ alkoxy group, including methoxy, ethoxy and propoxy, among which methoxy and ethoxy groups are preferred. More preferably, $R_2$ and $R_3$ are hydrogen atoms.

The acyl group represented by $R_4$ is preferably an acyl group derived from an aliphatic carboxylic acid, including acetyl and propionyl, among which acetyl group is preferred. The lower alkyl group represented by $R_4$ is the same as the above-described $R_1$.

The lower alkyl group represented by $R_5$ is the same as the above-described $R_1$, the optionally substituted lower alkyl group is a lower alkyl group optionally substituted with one to three hydroxy groups, halogen atoms (e.g., fluorine, chlorine, bromine and iodine) or the like, among which methyl and ethyl groups substituted with hydroxy group are preferred.

The lower alkyl group in Z is the same as the above-described $R_1$. Preferably, Z is sulfur atom.

Examples of the anion represented by $X^-$ are a halogen ion (fluoride, chloride, bromide and iodine ions), boron halide ion (e.g., $BF_4^-$, $BCl_4^-$ and $BBr_4^-$), phosphorus compound ion, halogeno oxyacid ion, fluorosulfuric acid ion, methylsulfuric acid ion and tetraphenylboron compound ion having a halogen in its aromatic ring or an alkyl group having a halogen as substituent, among which bromide ion and $BF_4^-$ are preferred.

The following are specific examples of the compound having the formula (I):

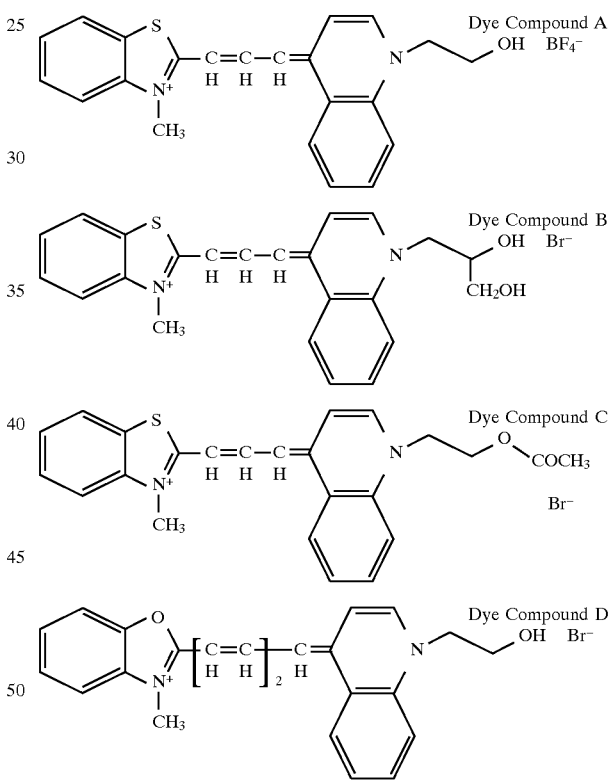

A compound having the formula (I) wherein n=1 may be obtained, for example, by reacting a compound represented by the formula (II):

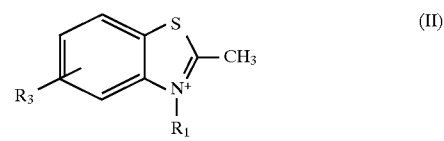

(II)

with a N,N-disubstituted formamidine, reacting the resultant with a quinoline derivative represented by the formula (III):

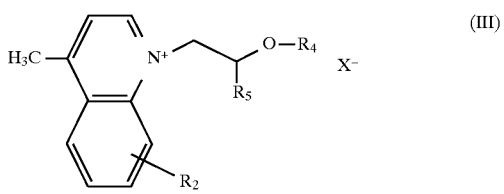

and then treating the resultant with sodium borofluoride or potassium bromide.

A compound having the formula (I) wherein n=2 may be obtained, for example, by using malonaldehyde bis (phenylimine) salt instead of the N,N-disubstituted formamidine in the above reaction.

In the compound of the formula (I), the polarity thereof may be raised by introducing a polar functional group such as hydroxy, hydroxyethyl or acetyl group in its molecule. Consequently, the bonding ability thereof to the lipid bilayer of erythrocyte cell membrane or the hydrophobic region of hemoglobin which have low polarity declines, and thus the non-specific dyeing of erythrocytes is considered to be inhibited.

The content of the above dye compound in the reagent according to the present invention is to be sufficient for dyeing reticulocytes and can be suitably adjusted depending on dyes and compositions of the reagent, for example, about 0.1 to 100 mg/liter, preferably 0.3 to 30 mg/liter. When the concentration of the dye exceeds 100 mg/liter, the non-specific fluorescence of erythrocytes increases generally, though it depends on the dye. Therefore, unpreferably, it becomes difficult to distinguish reticulocytes from erythrocytes. When the concentration of the dye is below 0.1 mg/liter, unpreferably the concentration of the dye is likely to drop due to the adsorption of the dye to a container wall, the decomposition of the dye and the like, even though the reagent can still be used.

The reagent for dyeing reticulocytes according to the present invention includes, in addition to the above compound, a multivalent anion for inhibiting erythrocytes from being dyed non-specifically and a buffer for maintaining pH. The reagent is further adjusted to have a physiological osmotic pressure (e.g., about 150 to 600 mOsm/kg).

The present inventors have found during their study of the composition of dyeing solution, that, when the principal ingredient of an osmotic pressure compensating agent in a conventional dyeing solution is NaCl (particularly Cl⁻), the non-specific fluorescence of erythrocytes increases and the specific fluorescence of reticulocytes decreases, so that it is more difficult to distinguish the reticulocytes from the erythrocytes. On the other hand, they have found that, when Cl⁻ in dyeing solution is substituted with a multivalent anion, the non-specific dyeing of erythrocytes is remarkably inhibited, so that it is easier to distinguish the reticulocytes from the erythrocytes. Accordingly, a multivalent anion is put into the reagent of the present invention. Particularly appropriate examples of the multivalent anion usable for this purpose are multivalent carboxylic acid ion such as citric acid and EDTA, or phosphoric, sulfuric ion or carbonate ion. The content of the multivalent anion is 50% or more, preferably 70% or more, with respect to the whole anion components contained in the reagent. The mechanism is not clear, but the multivalent anion has actual effect in increasing the specific fluorescence in a content within the above-mentioned range. The pair ion to the multivalent ion is not particularly limited, but an alkaline metal ion is preferred.

The buffer in the reagent of the present invention serves to maintain a constant pH in order to ensure stability in dyeing reticulocytes. The buffer is usually used in a concentration of above several mM to 100 mM. The kind of the buffer is not particularly limited provided that it is usually used. For example, carboxylic acids, phosphoric acid, Good's buffers, taurine or triethanolamine may be suitably chosen according to an appropriate pH. The pH, though it varies depending on dyes, may be within the range from 6.0 to 11.0, preferably from 7.0 to 10.0, more preferably from 8.0 to 9.5. When pH is lower than 6.0 or higher than 11.0, erythrocytes are liable to be lysed, which disadvantageously prevents accurate determination. Further, when the pH is too high, anion groups on erythrocyte cell membrane tend to dissociate and bond to the dye, which is cationic, so that, unpreferably, the non-specific fluorescence of erythrocytes increases and the erythrocytes cannot be easily distinguished from the reticulocytes. If the above-described multivalent anion is able to adjust pH of the reagent within an appropriate range, the multivalent anion may also serve as a buffer.

It is preferable that the reagent of the present invention is adjusted to have a physiological osmotic pressure in order to prevent hypotonic hemolysis of erythrocytes. Suitable osmotic pressure for that purpose is usually 150 mOsm/kg or higher. When the osmotic pressure is too high, no specific adverse effect may be seen. However, the osmotic pressure is usually adjusted up to about 600 mOsm/kg. For adjusting the osmotic pressure within the above range, an osmotic pressure compensating agent may be contained. As the osmotic pressure compensating agent, for example, an alkali metal salt of an organic acid such as propionic acid, and sugars such as glucose and mannose may be preferably used. Alternatively, alkali metal halide such as sodium chloride and alkali earth metal halide may be used unless they exceed 50% of the whole anionic components in the reagent. If the above-mentioned multivalent anion can adjust the osmotic pressure of the reagent within the appropriate range, no further osmotic pressure compensating agent is required to be added.

In the reagent of the present invention, a cationic surfactant may further be contained as a dyeing accelerator. The cationic surfactant includes a compound of the following structure:

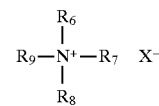

wherein $R_6$ is a $C_{8-12}$ alkyl group, $R_7$, $R_8$ and $R_9$ are lower alkyl groups and X is at least one selected from halogens.

The $C_{8-12}$ alkyl groups represented by $R_6$ include straight-chain and branched chain alkyl groups such as octyl, decyl and lauryl, among which octyl and decyl groups are preferred.

The lower alkyl groups represented by $R_7$, $R_8$ and $R_9$ include $C_{1-6}$ straight-chain and branched chain alkyl groups, among which methyl, ethyl and propyl groups are preferred. The halogens include fluorine, chlorine, bromine and iodine.

Examples of the cationic surfactant are octyltrimethylammonium bromide (OTAB), decyltrimethylammonium bromide (DTAB) and lauryltrimethylammonium chloride (LTAC).

The use amount of the cationic surfactant as dyeing accelerator is preferably, for example, 3000 to 20000 mg/liter for OTAB, 500 to 3000 mg/liter for DATB and 50 to 250 mg/liter for LTAC. The larger the number of the whole carbons, the smaller the effective amount. Use of the dyeing accelerator in large amount is not preferred because it lyses erythrocytes. The mechanism of the cationic surfactant is not clear, but it is considered that the cationic surfactant accelerates the penetration of the dye through erythrocyte cell membrane. Further, the cationic surfactant spheres erythrocytes and thus serves to converge distribution of the forward scattered light intensity of erythroid cells. Consequently, the platelets and erythrocytes can be easily detected. Also, surprisingly, it has been found possible to distinguish normocytes which are observed after treatment for microcytosis such as iron deficiency anemia, from microcytes resulted from the disease.

Figure 21:
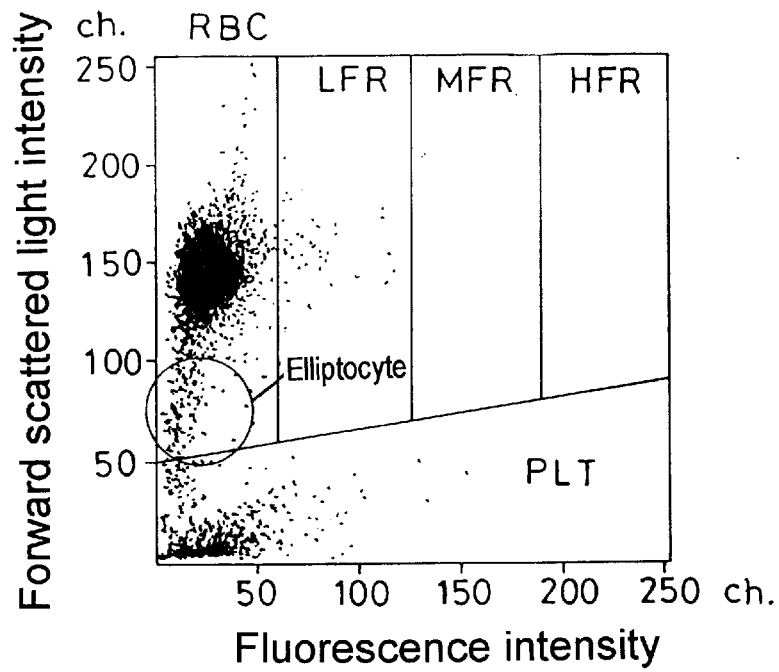
FIG. 21 is a scattergram of the forward scattered light intensity and the fluorescence intensity of blood of a patient suffering from anemia containing elliptocytes measured by the method of the present invention using a reagent for dyeing reticulocytes containing a Dye Compound A of the present invention.
Figure 22:
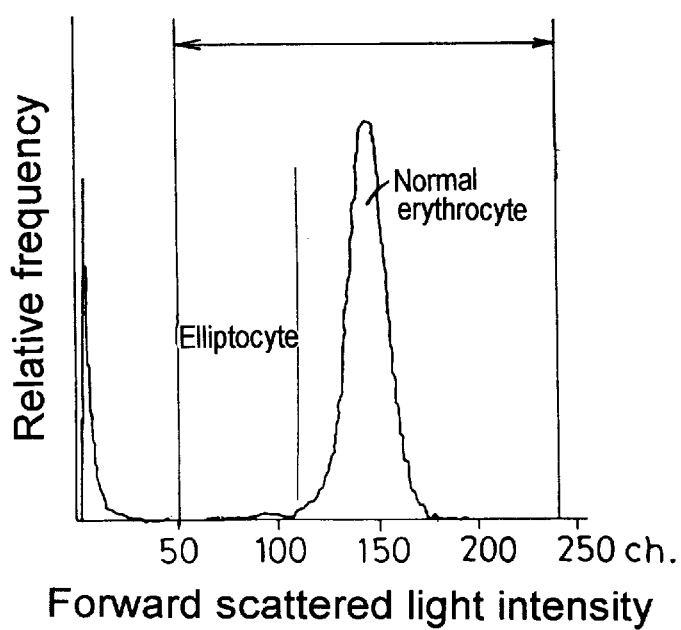
FIG. 22 is a distribution diagram of the forward scattered light intensity of blood of a patient suffering from anemia containing elliptocytes measured by the method of the present invention using a reagent for dyeing reticulocytes containing a Dye Compound A of the present invention.

Further, as shown in FIGS. 21 and 22, elliptocytes, which appears only in a small number, can be detected. Thus the convergence of the forward scattered light intensity distribution not only facilitates the determination of reticulocytes but also enables erythrocytes of abnormal shapes such as microcytes and elliptocytes to be detected.

The reagent of the present invention may contain other components than described above, for example, a preservative such as sodium 2-pyridylthio-1-oxide and β-phenethyl alcohol.

Further, when the compound of the present invention is unstable in aqueous solution, the compound may be dissolved and stored in an appropriate nonaqueous solvent such as ethanol, dimethyl sulfoxide and ethylene glycol, and mixed in use with an aqueous solution containing the other components.

In order to measure reticulocytes with a flow cytometer using the reagent of the present invention, the above reagent for dyeing reticulocytes is first mixed with a hematological sample to obtain a sample to be measured (subject sample) in step (i). The hematological sample here includes every kind of sample containing a blood component to be detected, for example, peripheral blood treated with anticoagulant and bone marrow fluid. In preparing the subject sample, the reagent for dyeing reticulocytes is preferably mixed and reacted with the hematological sample in a mixture ratio of 100:1 to 1000:1. The reaction temperature is preferably about 25° to 50° C., more preferably 35° to 45° C. The reaction time, though it varies to some extent depending on dyes contained in the reagent, is preferably 10 seconds to 5 minutes, more preferably 20 seconds to 2 minutes, still more preferable 20 to 60 seconds.

Figure 9:
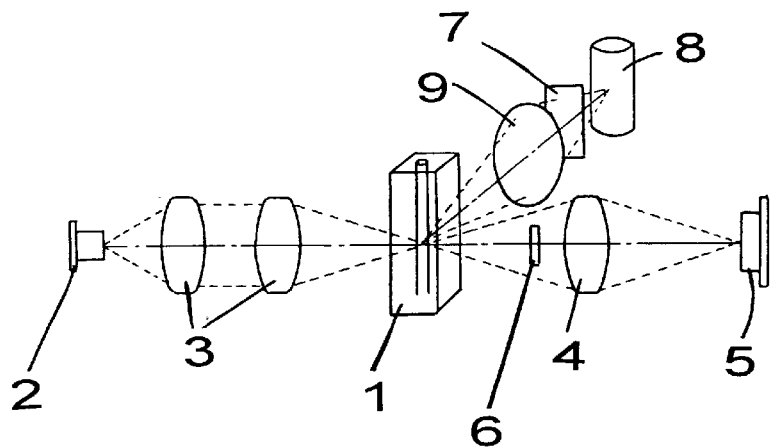
FIG. 9 is an optical portion of a flow cytometer provided with a red wavelength light source used in the method of the present invention.
Figure 10:
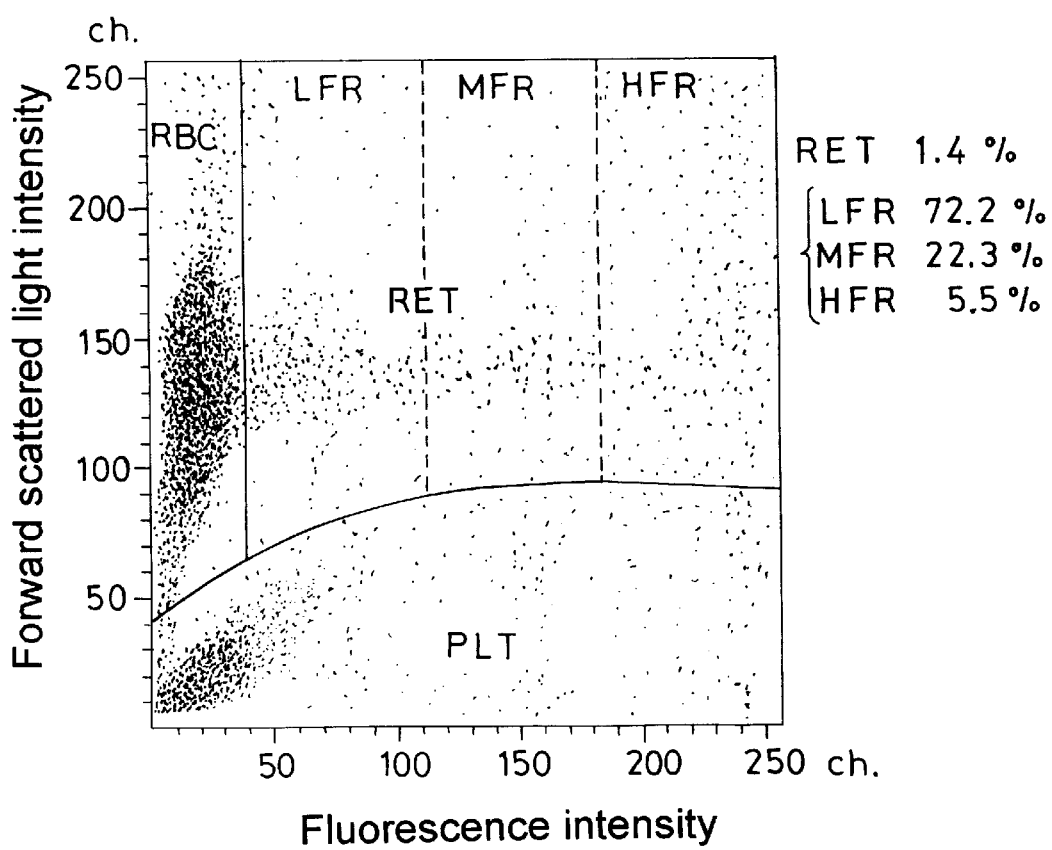
FIG. 10 is a scattergram of reticulocytes measured by a conventional R-series analyzer.

Then in step (ii), the subject sample as obtained above is introduced into a flowing system of the flow cytometer provided with a light source emitting red wavelength light. The light source emitting red wavelength light usable in the present invention is not particularly limited provided that it can emit light of a red wavelength near the excitation wavelength of a dye to be used, for example of about 600 to 680 nm. As the light source, a He—Ne laser or semiconductor laser emitting light within the red wavelength range may be used, for example. FIG. 9 shows an optical portion of a flow cytometer having a light source emitting such red wavelength light. A flow cell 1 is disposed in front of the semiconductor laser 2 with a beam-condensing lens system 3 therebetween. A lens for receiving the forward scattered light 4 and a photodiode 5 are disposed in front of the flow cell 1 with a beam stopper 6 therebetween. A band-pass filter 7 and a photoelectron multiplier 8 are disposed on the side of the flow cell 1 with a lens for receiving side fluorescence 9 therebetween. For other portions of the apparatus such as a portion for flowing the sample, a data processor and the like, a conventional structure (e.g. R-2000) may be modified and used (R-2000 provided with the optical portion shown in FIG. 9 will hereafter be referred to as modified R-2000).

Then in step (iii), the red wavelength light is emitted to cells flowing in a sheath flow by using the above-described red wavelength light source. In step (iv), the scattered light and fluorescence from the cells are measured. The scattered light here may be either forward scattered light or side scattered light. Further, the forward scattered light may be either forward high-angle (6° to 20°) scattered light or forward low-angle (1° to 5°) scattered light. The scattered light serves as a parameter indicating the size of a cell. Another parameter to indicate the size of a cell is electrical resistance signal, which may be combined with the above-described method, if required.

In step (v), the platelets and erythroid cells are distinguished by the scattered light intensity or by the scattered light intensity and the fluorescence intensity;

In step (vi), the erythrocytes, reticulocytes and leukocytes are distinguished by the fluorescence intensity or by the fluorescence intensity and the scattered light intensity. Then, in step (vii), the individual kinds of cells are classifying and counting and the percentages thereof are calculated.

EXAMPLES

Example 1

Preparation of Dye Compound A

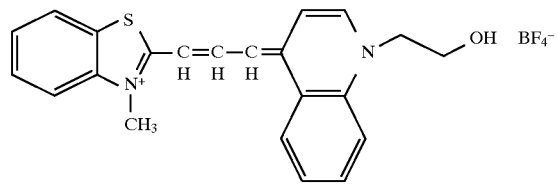

2,3-Dimethylbenzothiazolium methanesulfate (6.0 g) and N,N-diphenyl formamidine (12.8 g) in 120 ml of acetic acid were stirred for 1.5 hours in oil bath at 90° C. The reaction mixture was poured into 1.8 liters of hexane, and then the obtained red oil was further suspended and washed with 1.5 liters of hexane to remove the acetic acid. This crude product was recrystallized from ethyl acetate-hexane. The yield was 4.0 g (48%). To the product, 1-(2-hydroxy)ethyllepidinium bromide (3.1 g) and pyridine (80 ml) were added and stirred for 1.5 hours in oil bath at 90° C. To the reaction mixture, a solution of sodium borofluoride (1.27 g) in 9 ml of DMF was added. The mixture was stirred with heat for 15 minutes and then poured into 2 liters of ethyl acetate. The precipitates were taken by filtration. The yield was 5.0 g (100%). Dye Compound A was obtained as dark purple powders and its analytical data are shown as follows.

TLC (silica gel, ethanol-methylene chloride) Rf=0.2

$^1$H-NMR (DMSO-d6): δ ppm (TMS)

3.73 (s, 3H), 3.82 (t, 2H), 4.64 (t, 2H), 5.10 (s, 1H), 6.45 (d, 1H), 7.10 (d, 1H), 7.31 (t, 1H), 7.50–8.51 (m, 10H)

IR (cm$^{-1}$): 1625, 1560, 1520, 1490, 1450, 1400, 1320, 1260, 1220, 1150, 760

MASS (FAB positive): m/z=361

HPLC 95.9% (MeOH-35%SDSaq.soln.=80:20)

Absorption Maxima: 627 nm (methanol)

Example 2

Preparation of Dye Compound B

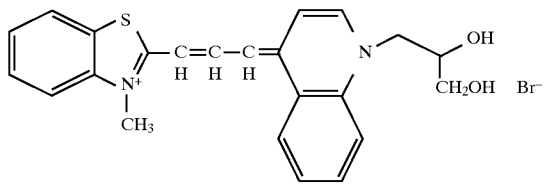

3-Methyl-2-methylbenzothiazolium methanesulfate (6.0 g) and N,N-diphenyl formamidine (12.8 g) in 120 ml of acetic acid were stirred for 1.5 hours in oil bath at 90° C. The reaction mixture was poured into 1.8 liters of hexane, and then the obtained red oil was further suspended and washed with 1.5 liters of hexane to remove the acetic acid. This crude product was recrystallized from ethyl acetate-hexane. The yield was 48%. To this, 1-(2,3-dihydroxy)propyllepidinium bromide (3.1 g) and pyridine (80 ml) were added and stirred for 1.5 hours in oil bath at 90° C. To the reaction mixture, a solution of sodium borofluoride (1.27 g) in 9 ml of DMF was added. The mixture was stirred with heat for 15 minutes and then poured into 2 liters of ethyl acetate. The precipitates were taken by filtration. The yield was 180 mg (31%). Dye Compound B was obtained as dark purple powders and its analytical data are as follows.

TLC (silica gel, methanol-methylene chloride) Rf=0.15

$^1$H-NMR (DMSO-d6): δ ppm (TMS)

3.73 (s, 3H), 3.88 (m, 2H), 4.80 (m, 1H), 5.36 (d, 2H), 6.45 (d, 1H), 7.10 (d, 1H), 7.31 (t, 1H), 7.50–8.51 (m, 10H), 9.27 (s, 2H)

IR (cm$^{-1}$): 1620, 1560, 1520, 1480, 1450, 1400, 1310, 1250, 1210, 1150, 740

MASS (FAB positive): m/z=391

Absorption Maxima: 628 nm (methanol)

Example 3

Preparation of Dye Compound C

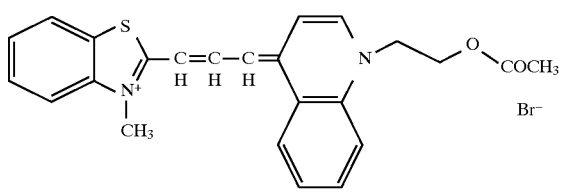

1-Hydroxyethyllepidinium bromide (5 g) and N,N-diphenyl formamidine (4.6 g) in 100 ml of acetic anhydride were stirred for 1.5 hours in oil bath at 90° C. The reaction mixture was concentrated and poured into 0.5 liters of hexane to remove the acetic anhydride. This crude product was purified by a silica gel column (methanol-methylene chloride). The yield was 8.4 g (100%). This product (3.0 g) were suspended in 100 ml of pyridine and heated in oil bath at 90° C., to which 2,3-dimethylbenzothiazolium methanesulfate (3.4 g) was added. The mixture was stirred for 1.5 hours at 90° C., then concentrated, washed with ether and hexane, and purified by silica gel column (methanol-methylene chloride). The yield was 0.5 g (17%). Dye Compound C was obtained as dark purple powders. Its analytical data are as follows.

TLC (silica gel, methanol-methylene chloride) Rf=0.4

$^1$H-NMR (DMSO-d6): δ ppm (TMS)

1.93 (s, 3H), 3.77 (s, 3H), 4.45 (t, 2H), 4.80 (t, 2H), 6.55 (d, 1H), 7.10 (d, 1H), 7.37 (t, 1H), 7.53–8.47 (m, 10H)

IR (cm$^{-1}$): 1740, 1620, 1560, 1520, 1480, 1450, 1400, 1310, 1250, 1200, 1150, 1080, 740

MASS (FAB positive): m/z=403

Absorption Maxima: 631 nm (methanol)

Example 4

Preparation of Dye Compound D

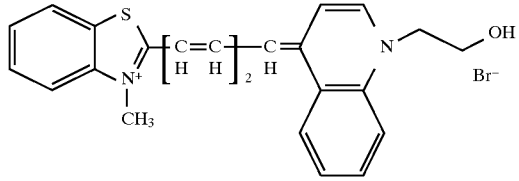

3-Methyl-2-methylbenzooxazolium methanesulfate (250 mg) and malonaldehyde bis(phenylimine) hydrochloride (250 mg) in 100 ml of acetic anhydride were stirred for 0.5 hours in oil bath at 125° C. The reaction mixture was cooled and then ether was added thereto. The crystal was taken by filtration (the yield being 45%), to which 1-(2-hydroxy)ethyllepidinium bromide (150 mg) and pyridine (5 ml) were added. The mixture was stirred for 0.5 hours in oil bath at 125° C., and then concentrated. The object was extracted with methylene chloride (the yield being 20%). Dye Compound D was obtained as dark purple powders and its analytical dada are as follows.

TLC (silica gel, 10% ethanol-methylene chloride) Rf=0.20

$^1$H-NMR (DMSO-d6): δ ppm (TMS)

3.73 (s, 3H), 3.82 (t, 2H), 4.64 (t, 2H), 5.10 (s, 1H), 6.45–7.31 (m, 5H), 7.50–8.51 (m, 10H)

IR (cm$^{-1}$): 1625, 1560, 1520, 1490, 1450, 1400, 1320, 1260, 1220, 1150, 760

MASS (FAB positive): m/z=371

Absorption spectrum: 693 nm (methanol)

Example 5

A reagent for dyeing reticulocytes having the following composition was prepared.

| | |
|---|---|
| Dye Compound A | 3.0 mg |
| Tricin (buffer) | 1.79 g |
| Trisodium citrate dianhydride (multivalent anion) | 29.4 g |
| Purified water | 1 liter |
| (adjusted to pH9.0 with NaOH) | |

To this reagent (2 ml), blood (10 μl) treated with an anticoagulant was added and incubated at 40° C. for 120 seconds to prepare a subject sample. The forward low-angle scattered light intensity and the fluorescence intensity of the subject sample were measured by use of a modified R-2000 The scattergram shown in FIG. 1 was obtained. The ratio of reticulocytes (RET) to the whole erythrocytes was 2.90%. The RET percentage measured by the conventional R-2000 was 2.70%.

Example 6

A reagent for dyeing reticulocytes having the following composition was prepared.

| | |
|---|---|
| Dye Compound A | 3.0 mg |
| Tricin (buffer) | 1.79 g |
| Trisodium citrate dianhydride (multivalent anion) | 29.4 g |
| LTAC (cationic surfactant, dyeing accelerator) | 150 mg |
| Purified water | 1 liter |
| (adjusted to pH9.0 with NaOH) | |

Figure 2:
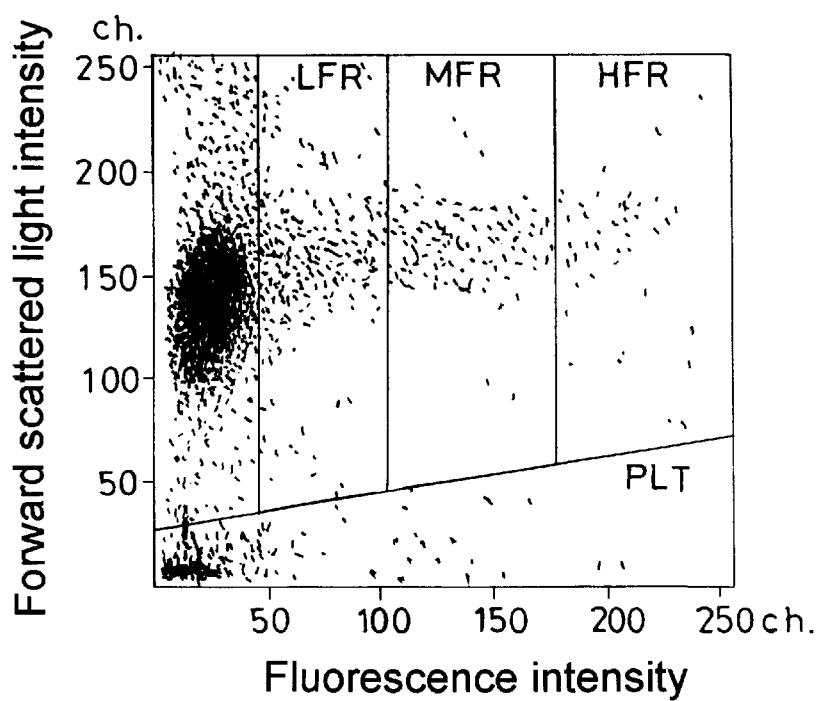
FIG. 2 shows a scattergram of the forward scattered light intensity and the fluorescence intensity of a hematological sample measured using a reagent for dyeing reticulocytes containing Dye Compound A of the present invention and a cationic surfactant.

To this reagent (2 ml), blood (10 μl) treated with an anticoagulant was added and incubated at 40° C. for 40 seconds. Then the forward low-angle scattered light intensity and the fluorescence intensity of this subject sample were measured in the same manner as described in the above Example 5. The scattergram shown in FIG. 2 was obtained. The ratio of reticulocytes (RET) to the whole erythrocytes was 2.72%. The RET percentage measured by the conventional R-2000 was 2.70%.

In this example, the subject sample was able to be prepared in a shorter time (one-third) than in Example 5, and the forward scattered light intensity distribution was converged due to the sphered erythrocytes, so that the distinction of the erythrocytes from the platelets was facilitated.

Example 7

A reagent for dyeing reticulocytes having the following composition was prepared.

| | |
|---|---|
| Dye Compound B | 30.0 mg |
| Taurin (buffer) | 1.25 g |
| Ethylenediaminetetraacetic acid, disodium salt dihydrate (multivalent anion) | 26.9 g |
| DTAB (cationic surfactant, dyeing accelerator) | 1.00 g |
| Purified water | 1 liter |
| (adjusted to pH9.0 with NaOH) | |

Figure 3:
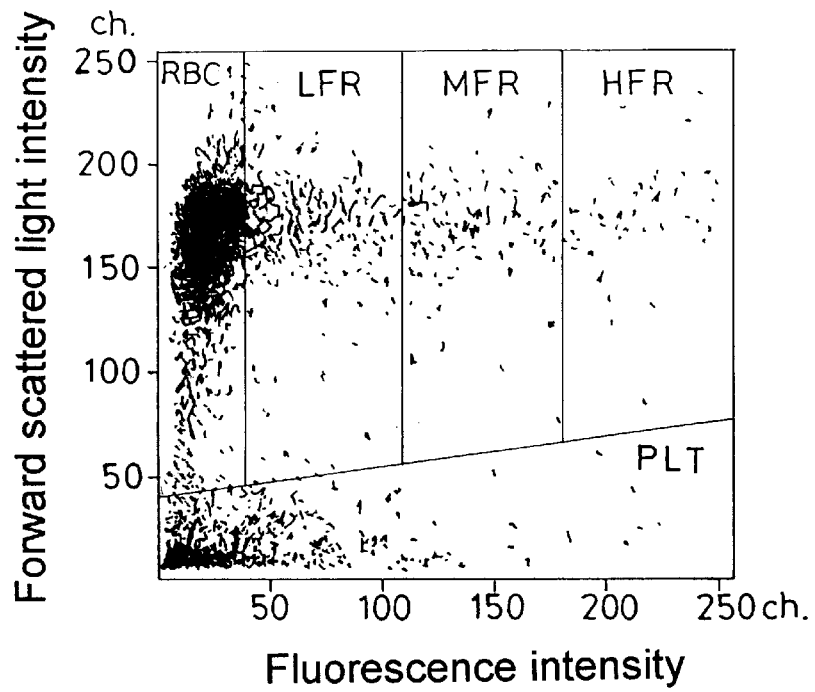
FIG. 3 shows a scattergram of the forward scattered light intensity and the fluorescence intensity of a hematological sample measured using a reagent for dyeing reticulocytes containing a Dye Compound B of the present invention.

To this reagent (2 ml), blood (10 μl) treated with an anticoagulant was added and incubated at 40° C. for 40 seconds. The forward low-angle scattered light intensity and the fluorescence intensity of the subject sample were measured in the same manner as described in Example 5. The scattergram shown in FIG. 3 was obtained. The ratio of reticulocytes (RET) to the whole erythrocytes was 2.82%. The RET percentage measured by the conventional R-2000 was 2.70%.

Example 8

A reagent for dyeing reticulocytes having the following composition was prepared.

| | |
|---|---|
| Dye Compound C | 1.0 mg |
| TAPS (buffer) | 2.43 g |
| Sodium dihydrogenphosphate dodecaanhydride (multivalent anion) | 35.8 g |
| DTAB (cationic surfactant, dyeing accelerator) | 1.00 g |
| Purified water | 1 liter |
| (adjusted to pH8.5 with NaOH) | |

Figure 4:
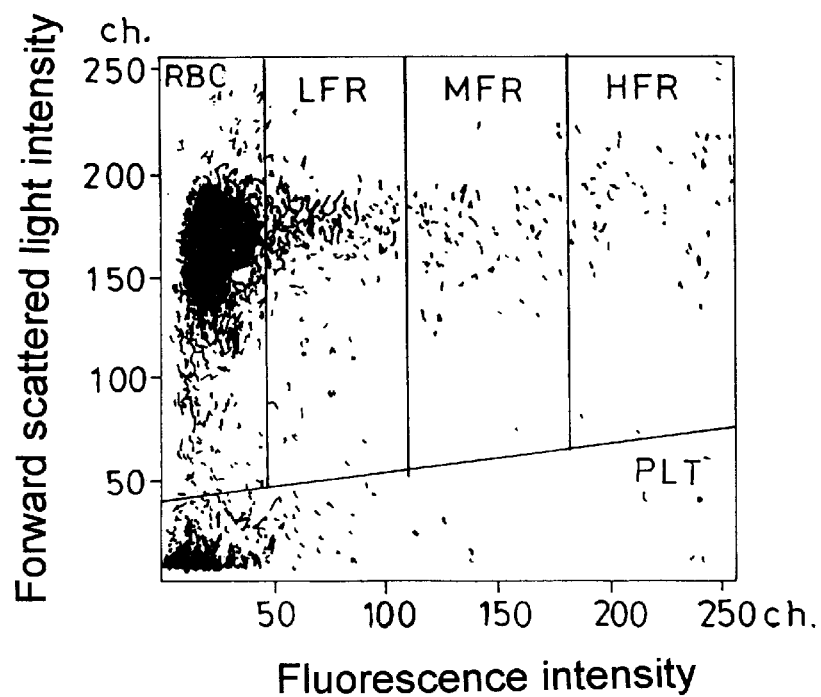
FIG. 4 shows a scattergram of the forward scattered light intensity and the fluorescence intensity of a hematological sample measured using a reagent for dyeing reticulocytes containing a Dye Compound C of the present invention.
Figure 5:
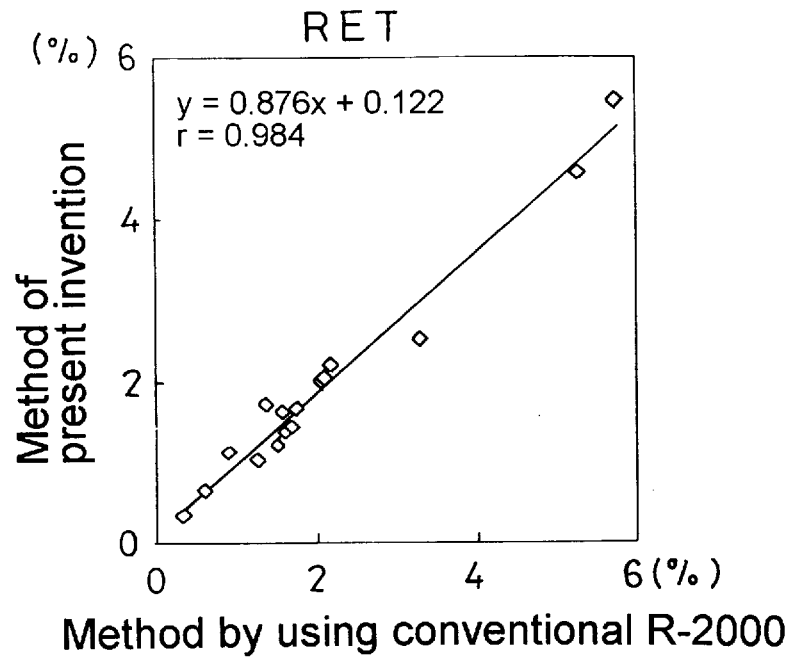
FIG. 5 shows correlation of RETs measured by the method of the present invention and by the conventional R-2000, a reagent for dyeing reticulocytes containing a Dye Compound A of the present invention being used in both the methods.
Figure 6:
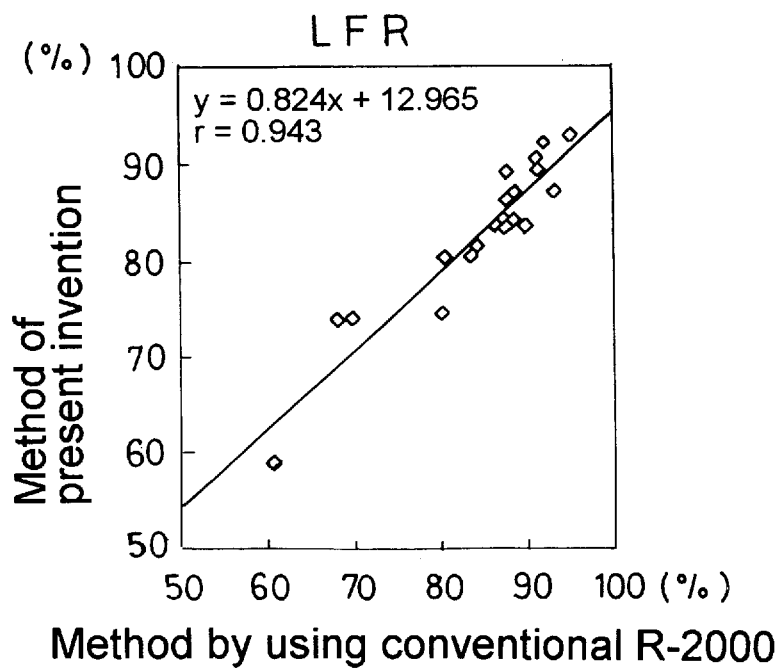
FIG. 6 shows correlation of LFRs measured by the method of the present invention and by the conventional R-2000, a reagent for dyeing reticulocytes containing a Dye Compound A of the present invention being used in both the methods.
Figure 7:
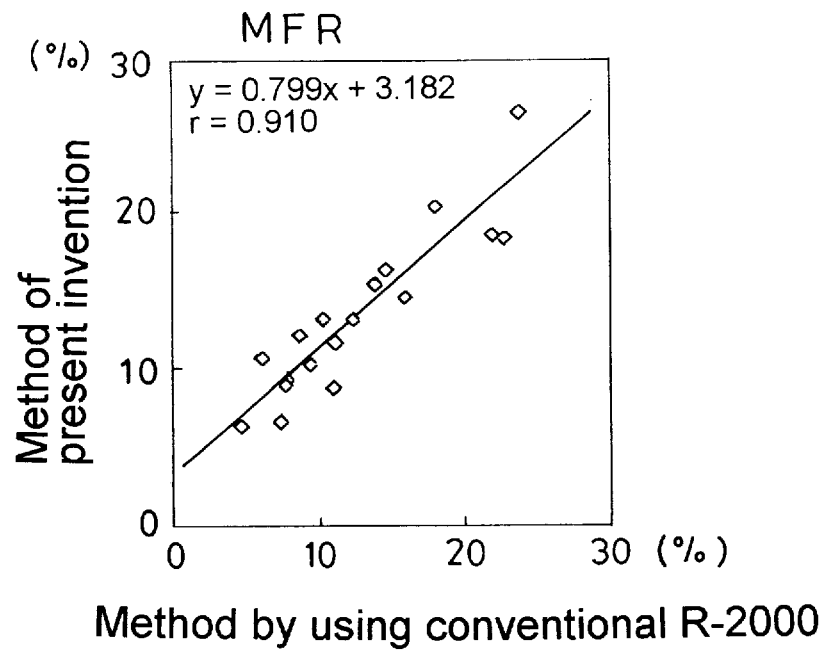
FIG. 7 shows correlation of MFRs measured by the method of the present invention and by the conventional R-2000, a reagent for dyeing reticulocytes containing a Dye Compound A of the present invention being used in both the methods.
Figure 8:
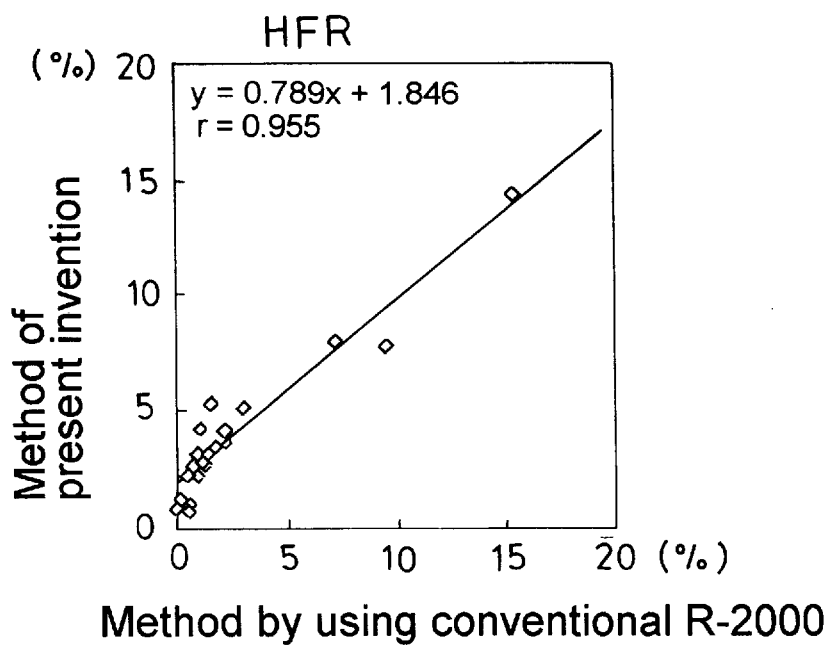
FIG. 8 shows correlation of HFRs measured by the method of the present invention and by the conventional R-2000, a reagent for dyeing reticulocytes containing a Dye Compound A of the present invention being used in both the methods.

To this reagent (2 ml), blood (10 μl) treated with an anticoagulant was added and incubated at 40° C. for 40 seconds. The forward low-angle scattered light intensity and the fluorescence intensity of the subject sample were measured in the same manner as described in Example 5. The scattergram shown in FIG. 4 was obtained. The ratio of reticulocytes (RET) to the whole erythrocytes was 2.50%. The RET percentage measured by the conventional R-2000 was 2.70%.

Example 9

A reagent for dyeing reticulocytes having the following composition was prepared.

| | |
|---|---|
| Dye Compound A | 3.0 mg |
| Tricin (buffer) | 1.79 g |
| Trisodium citrate dianhydride (multivalent anion) | 29.4 g |
| DTAB (cationic surfactant, dyeing accelerator) | 1000 mg |
| Purified water | 1 liter |
| (adjusted to pH9.0 with NaOH) | |

To this reagent (2 ml), blood (10 μl) treated with an anticoagulant was added and incubated at 40° C. for 40 seconds. Then the forward low-angle scattered light intensity and the fluorescence intensity of the subject sample were measured in the same manner as described in Example 5. This blood was also measured by the conventional R-2000. These determination results were compared and correlations of RETs, LFRs, MFRs and HFRs are shown in FIGS. 5, 6, 7 and 8 respectively. Referring to FIGS. 5 to 8, in the determination of reticulocytes by use of the reagent of the present invention and the small-sized semiconductor laser, better correlation is observed than in the determination by use of the conventional R-2000, particularly because the fluorescence intensity differs sufficiently between the mature erythrocytes and the reticulocytes. Therefore, it is considered that the method of the present invention is as efficient as that using a conventional apparatus and can detect reticulocytes accurately.

Example 10

Measured in the manner as described in Example 9 were blood samples of a normal person, a patient under medical treatment for iron deficiency anemia and a patient suffering from anemia having elliptocytes, after being treated with an anticoagulant.

Figure 11:
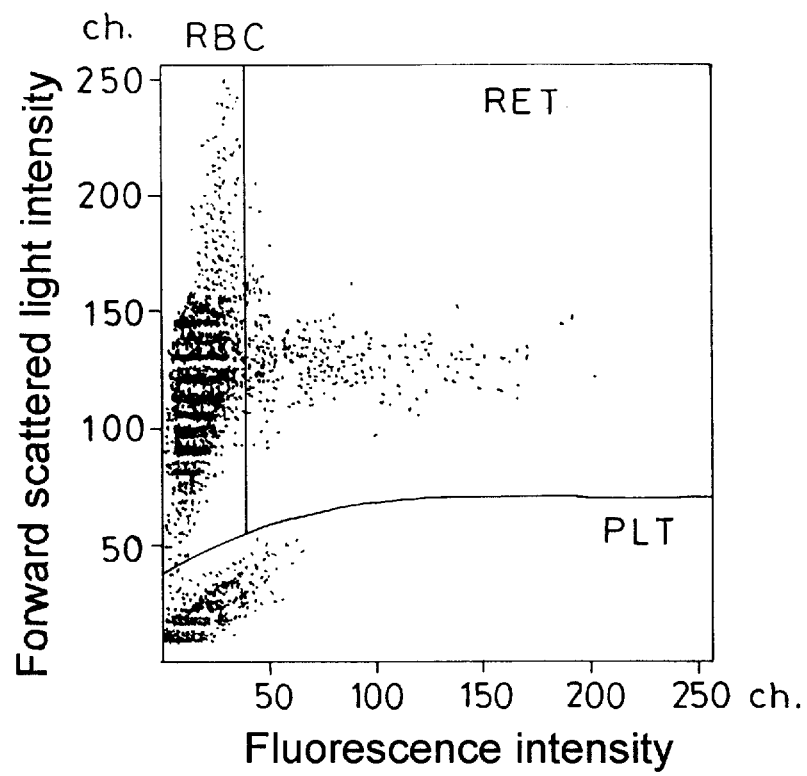
FIG. 11 is a scattergram of the forward scattered light intensity and the fluorescence intensity of blood of a normal person measured by the conventional R-2000.
Figure 12:
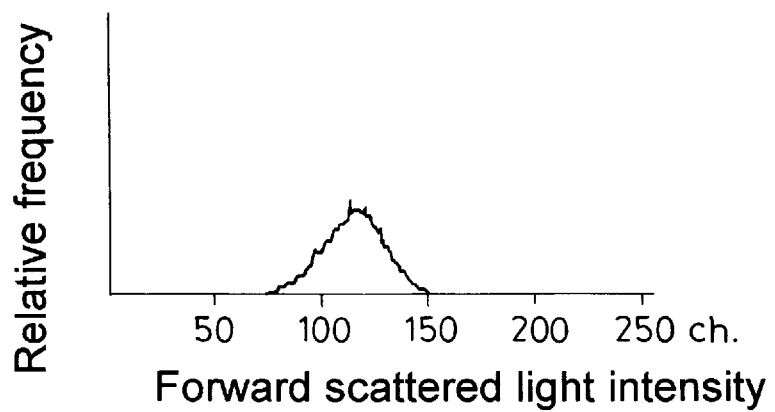
FIG. 12 is a distribution diagram of the forward scattered light intensity of blood of a normal person measured by the conventional R-2000.
Figure 13:
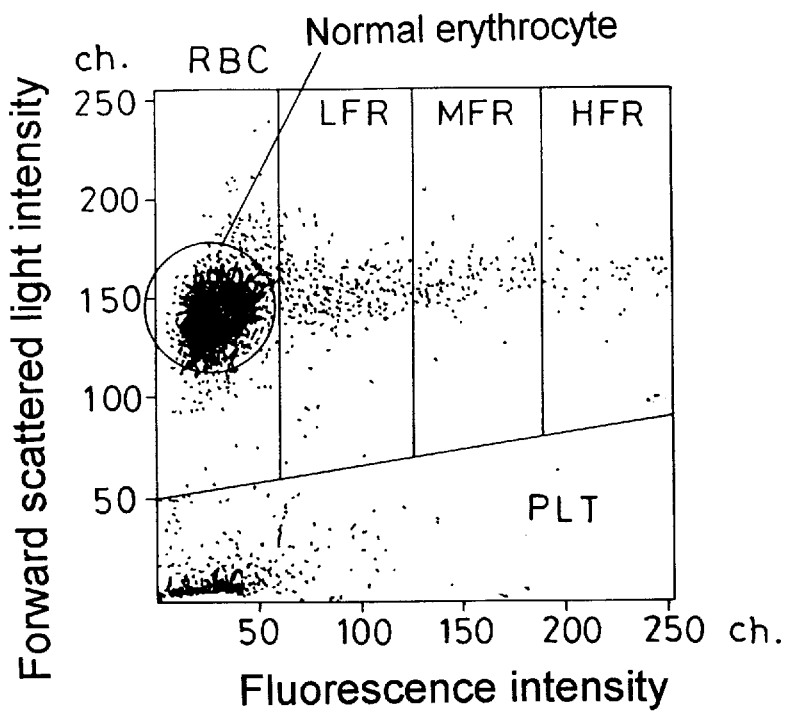
FIG. 13 is a scattergram of the forward scattered light intensity and the fluorescence intensity of blood of a normal person measured by the method of the present invention using a reagent for dyeing reticulocytes containing a Dye Compound A of the present invention.
Figure 14:
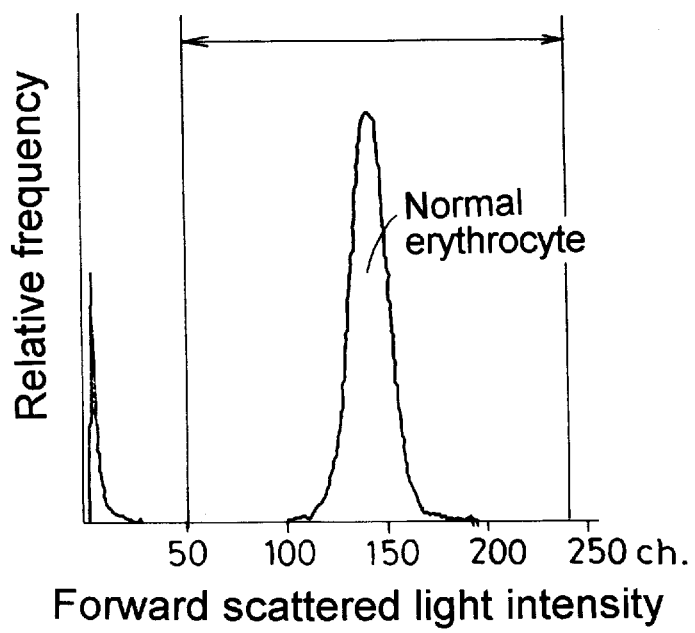
FIG. 14 is a distribution diagram of the forward scattered light intensity of blood of a normal person measured by the method of the present invention using a reagent for dyeing reticulocytes containing a Dye Compound A of the present invention.

The results on the normal person are shown in FIGS. 11 to 14. FIGS. 11 and 12 show the results measured by R-2000 and FIGS. 13 and 14 show the results measured by the method of the example. FIGS. 12 and 14 show distribution diagrams of the forward scattered light intensity.

Figure 15:
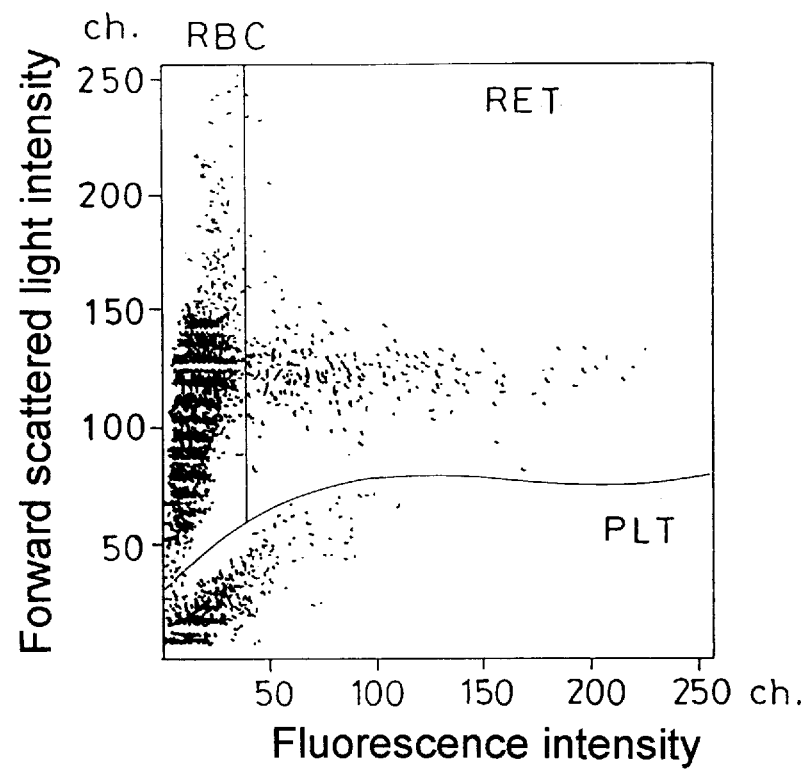
FIG. 15 is a scattergram of the forward scattered light intensity and the fluorescence intensity of blood of a patient under medical treatment for iron deficiency anemia measured by the conventional R-2000.
Figure 16:
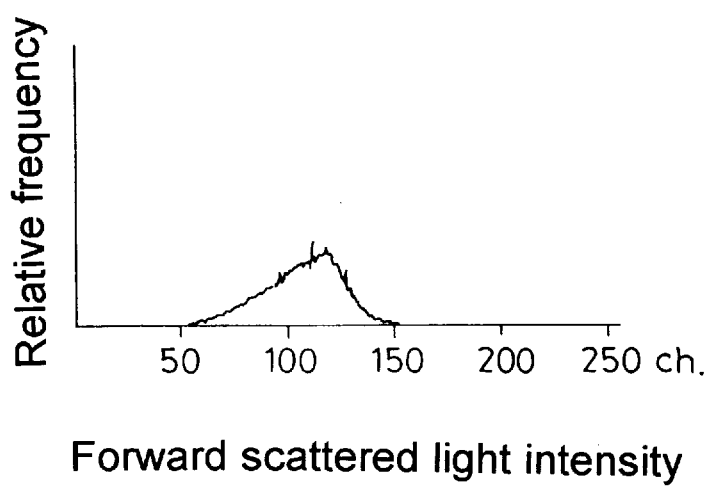
FIG. 16 is a distribution diagram of the forward scattered light intensity of blood of a patient under medical treatment for iron deficiency anemia measured by the conventional R-2000.
Figure 17:
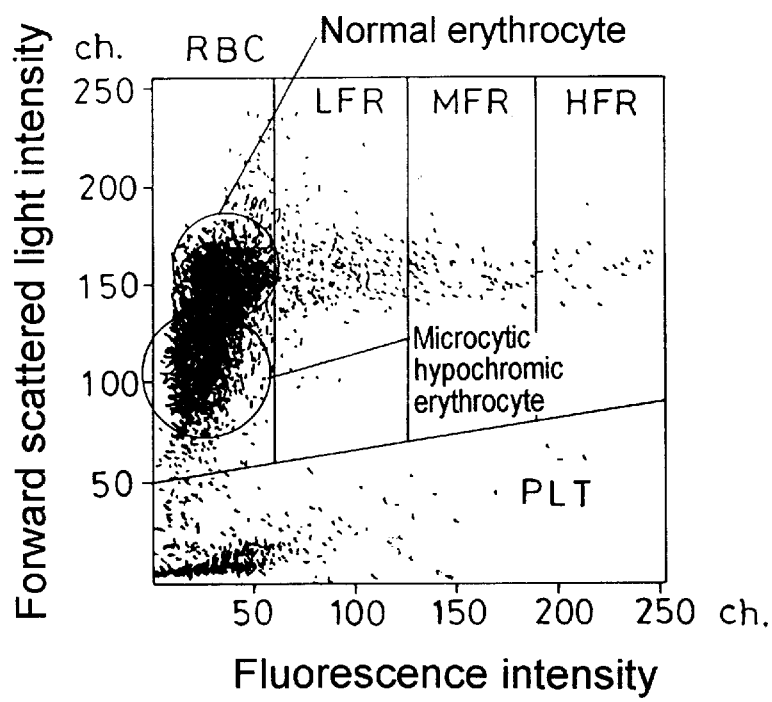
FIG. 17 is a scattergram of the forward scattered light intensity and the fluorescence intensity of blood of a patient under medical treatment for iron deficiency anemia measured by the method of the present invention using a reagent for dyeing reticulocytes containing a Dye Compound A of the present invention.
Figure 18:
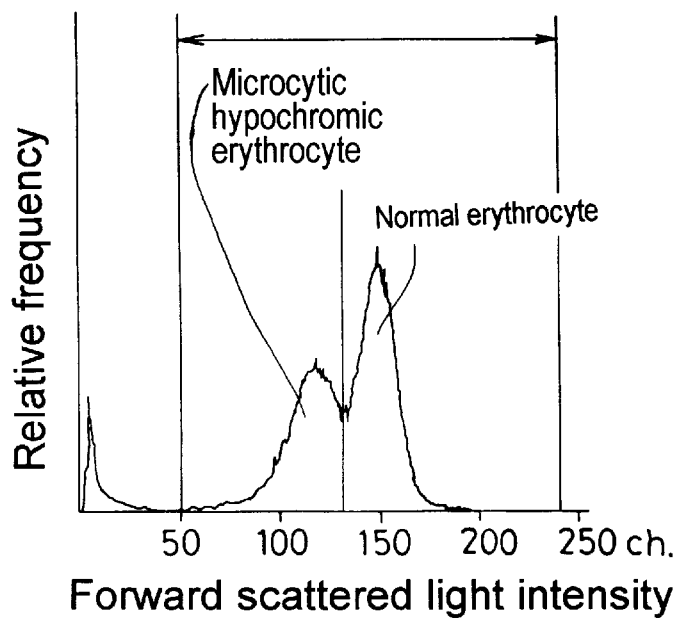
FIG. 18 is a distribution diagram of the forward scattered light intensity of blood of a patient under medical treatment for iron deficiency anemia measured by the method of the present invention using a reagent for dyeing reticulocytes containing a Dye Compound A of the present invention.

The results on the patient under medical treatment for iron deficiency anemia are shown in FIGS. 15 to 18. FIGS. 15 and 16 show the results measured by R-2000 and FIGS. 17 and 18 show the results measured by the method of the example. FIGS. 16 and 18 show distribution diagrams of the forward scattered light intensity. Referring to FIGS. 17 and 18, especially FIG. 18, microcytic, hypochromic erythrocytes resulted from the disease are clearly distinguished from normal erythrocytes resulted from the treatment. The conventional method, as shown in FIGS. 15 and 16, cannot distinguish them clearly.

Figure 19:
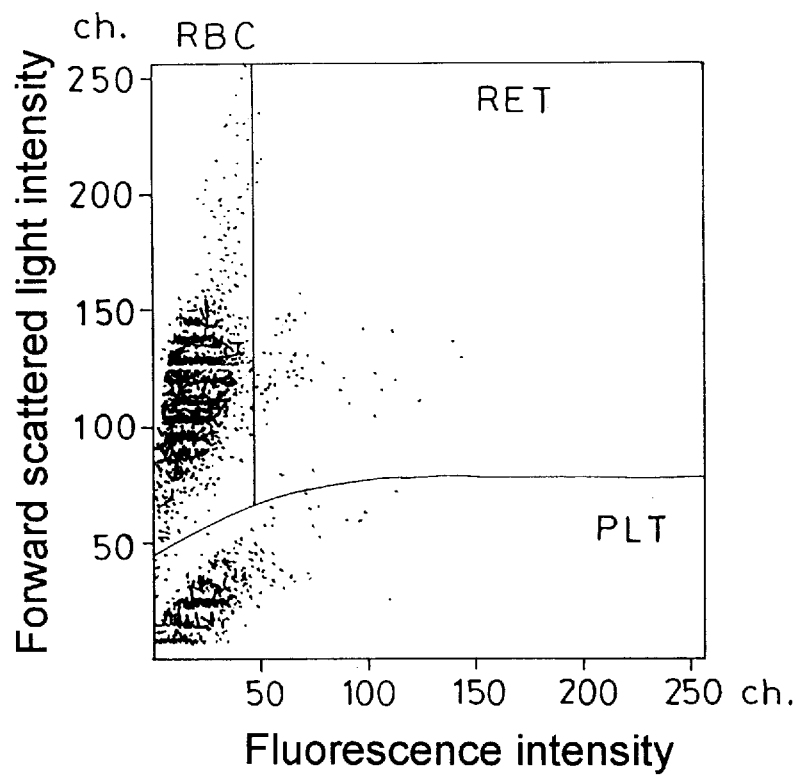
FIG. 19 is a scattergram of the forward scattered light intensity and the fluorescence intensity of blood of a patient suffering from anemia containing elliptocytes measured by the conventional R-2000.
Figure 20:
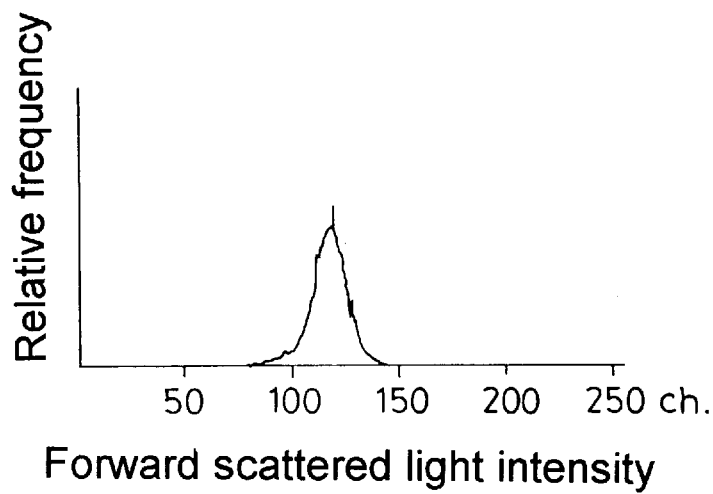
FIG. 20 is a distribution diagram of the forward scattered light intensity of blood of a patient suffering from anemia containing elliptocytes measured by the conventional R-2000.
Figure 23:
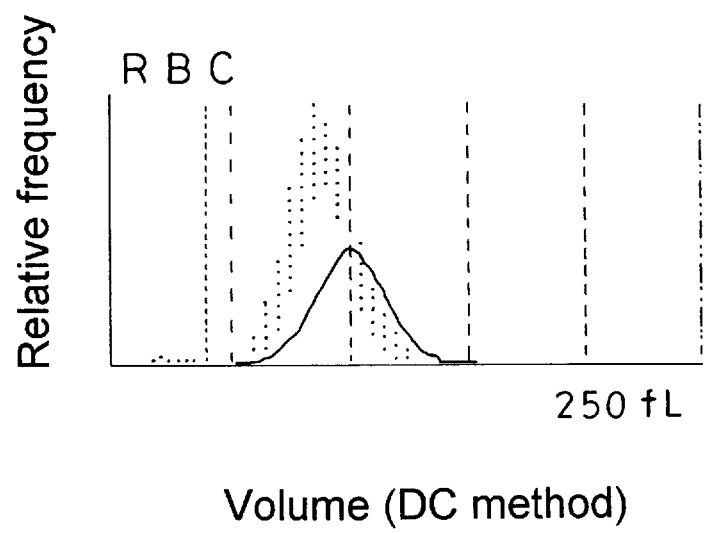
FIG. 23 is a diagram showing erythrocyte size distribution of blood of a patient suffering from anemia containing elliptocytes measured by the conventional electrical impedance detection.

The results on the patient suffering from anemia having elliptocytes are shown in FIGS. 19 to 23. FIGS. 19 and 20 show the results measured by R-2000 and FIGS. 21 and 22 show the results measured by the method of the example. FIGS. 20 and 22 show distribution diagrams of the forward scattered light intensity. FIG. 23 shows an erythrocyte size distribution diagram obtained by an electric impedance detector (SE-9000 manufactured by Toa Medical Electronics Co., Ltd.). Referring to FIGS. 21 and 22, especially FIG. 22, a group of elliptocytes are clearly distinguished. The conventional method shown in FIGS. 19 and 20 cannot distinguish them clearly. The erythrocyte size distribution obtained by the conventional electric impedance detection shown in FIG. 23 cannot detect the presence of elliptocytes, either.

The present invention not only has realized reduction in costs of the reticulocyte determination, that is reduction in costs of apparatus by using a small-sized semiconductor red-light laser, but also has allowed accurate determination of reticulocytes by use of red wavelength light. That is to say, the present invention has enabled determination of accuracy equal to or higher than that obtained by the conventionally used apparatus, R series, which uses expensive argon lasers (and Auramine O as dye).

Further, when the reagent of the present invention is used in combination with a cationic surfactant as dyeing accelerator, it has become possible to distinguish normacytes (normal erythrocytes) owing to medical treatment for microcytosis such as iron deficiency anemia from microcytes resulted from the disease and to detect erythrocytes of abnormal shape such as elliptocytes as well as to measure reticulocytes.

What is claimed is:

1. A fluorescent compound represented by the formula (Ia):

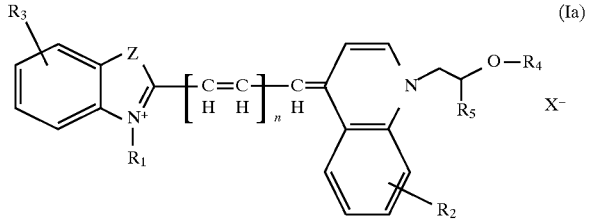

wherein $R_1$ is methyl; $R_2$ and $R_3$ are hydrogen atoms; and wherein, $R_4$ and $R_5$ are hydrogen atoms, n=1, X is a halogen atom, and Z is a sulfur atom; or $R_4$ and $R_5$ are hydrogen atoms, n=2, X is a halogen atom, and Z is an oxygen atom; or $R_4$ is hydrogen atom, $R_5$ is hydroxymethyl, n=1, X is a halogen atom, and Z is a sulfur atom; or $R_4$ is an acetyl group, $R_5$ is hydrogen atom, n=1, X is a halogen atom, and Z is a sulfur atom.

2. A reagent for dyeing reticulocytes comprising a compound represented by the formula (Ia) of claim 1.

3. A reagent for dyeing reticulocytes comprising (1) a fluorescent compound represented by formula (I):

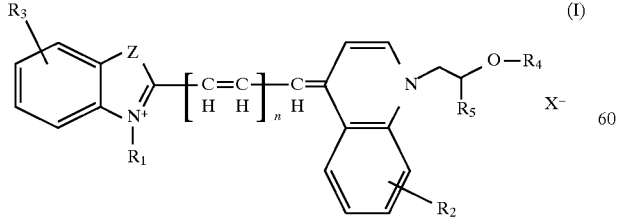

wherein $R_1$ is hydrogen atom or a lower alkyl group; $R_2$ and $R_3$ are independently hydrogen atom, a lower alkyl group or a lower alkoxy group; $R_4$ is hydrogen atom, an acyl group or a lower alkyl group; $R_5$ is hydrogen atom or an optionally substituted lower alkyl group; Z is sulfur atom, oxygen atom or carbon atom substituted with a lower alkyl group; n is 1 or 2; and $X^-$ is an anion, (2) a multivalent anion for inhibiting non-specific dyeing of erythrocytes and (3) a buffer.

4. A reagent according to claim 3 wherein the multivalent anion is at least one selected from the group consisting of sulfuric ion, phosphoric ion and multivalent carboxylic acid ion.

5. A reagent according to claim 3 which has a pH of 6.0 to 11.0.

6. A reagent according to claim 3 further comprising a cationic surfactant as a dyeing accelerator.

7. A reagent according to claim 6 in which the cationic surfactant has the formula:

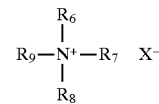

wherein $R_6$ is a $C_{8-12}$ alkyl group; $R_7$, $R_8$ and $R_9$ are lower alkyl groups; and X is a halogen atom.

8. A reagent according to claim 6 wherein the cationic surfactant is at least one selected from the group consisting of lauryltrimetylammonium chloride, decyltrimetylammonium bromide and octyltrimetylammonium bromide.

9. A reagent according to claim 3 comprising (i) a fluorescent compound of the formula (I) in a concentration of 0.1–100 mg/l, (ii) a multivalent anion providing 50% or more of whole anions in the reagent, (iii) a buffer and (iv) an osmotic pressure compensating reagent in an amount sufficient for maintaining an osmotic pressure of 150 to 600 m Osm/kg.

10. A reagent for dyeing reticulocytes comprising (1) a fluorescent compound represented by formula (I):

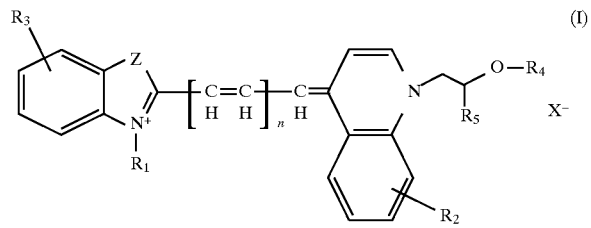

wherein $R_1$ is hydrogen atom or a lower alkyl group; $R_2$ and $R_3$ are independently hydrogen atom, a lower alkyl group or a lower alkoxy group; $R_4$ is hydrogen atom, an acyl group or a lower alkyl group; $R_5$ is hydrogen atom or an optionally substituted lower alkyl group; Z is sulfur atom, oxygen atom or carbon atom substituted with a lower alkyl group; n is 1 or 2; and $X^-$ is an anion, and (2) a cationic surfactant as a dyeing accelerator.

11. A reagent according to claim 10 in which the cationic surfactant has the formula:

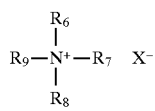

wherein $R_6$ is a $C_{8-12}$ alkyl group; $R_7$, $R_8$ and $R_9$ are lower alkyl groups; and X is a halogen atom.

12. A reagent according to claim 10 wherein the cationic surfactant is at least one selected from the group consisting of lauryltrimetylammonium chloride, decyltrimetylammonium bromide and octyltrimetylammonium bromide.

13. A reagent according to claim 10 comprising (i) a fluorescent compound of the formula (I) in a concentration of 0.1–100 mg/l, (ii) a multivalent anion providing 50% or more of whole anions in the reagent, (iii) a buffer and (iv) an osmotic pressure compensating reagent in an amount sufficient for maintaining an osmotic pressure of 150 to 600 m Osm/kg.

* * * * *